United States Patent
Warier et al.

(10) Patent No.: US 11,521,321 B1
(45) Date of Patent: Dec. 6, 2022

(54) MONITORING COMPUTED TOMOGRAPHY (CT) SCAN IMAGE

(71) Applicant: Qure.ai Technologies Private Limited, Mumbai (IN)

(72) Inventors: Prashant Warier, Mumbai (IN); Ankit Modi, Koderma (IN); Preetham Putha, Guntur (IN); Prakash Vanapalli, Vishakapatnam (IN); Vikash Challa, Vizianagaram (IN)

(73) Assignee: QURE.AI TECHNOLOGIES PRIVATE LIMITED, Mumbai (IN)

( * ) Notice: Subject to any disclaimer, the term of this patent is extended or adjusted under 35 U.S.C. 154(b) by 0 days.

(21) Appl. No.: 17/457,465

(22) Filed: Dec. 3, 2021

(30) Foreign Application Priority Data

Oct. 7, 2021 (IN) .............................. 202121045730

(51) Int. Cl.
    *G06T 7/00*     (2017.01)
    *G06T 7/62*     (2017.01)
    (Continued)

(52) U.S. Cl.
CPC ............ *G06T 7/0016* (2013.01); *A61B 6/032* (2013.01); *A61B 6/50* (2013.01); *A61B 6/5217* (2013.01); *A61B 6/5223* (2013.01); *A61B 6/5258* (2013.01); *G06T 5/002* (2013.01); *G06T 7/11* (2017.01); *G06T 7/40* (2013.01); *G06T 7/62* (2017.01); *G06V 10/25* (2022.01);
(Continued)

(58) Field of Classification Search
CPC . G06T 7/0016; G06T 7/62; G06T 7/11; G06T 5/002; G06T 7/40; G06T 2207/10081; G06T 2207/20081; G06T 2207/20084; G06T 2207/30064; G06T 2207/10072; G06T 2207/30061; G06T 11/001; G16H 50/30; G16H 50/20; G16H 30/40; G06V 10/25; G06V 10/75; G06V 10/82; G06V 10/273; A61B 6/032; A61B 6/50; A61B 6/5217; A61B 6/5223; A61B 6/5258
See application file for complete search history.

(56) References Cited

U.S. PATENT DOCUMENTS 6,738,499 B1 * 5/2004 Doi ....................... G06T 7/0012
    382/128
2004/0252870 A1 * 12/2004 Reeves ................... G06T 5/002
    382/128
(Continued)

*Primary Examiner* — Vu Le
*Assistant Examiner* — Winta Gebreslassie
(74) *Attorney, Agent, or Firm* — FisherBroyles, LLP; Susan M. Oiler

(57) ABSTRACT

Disclosed is a system and a method for monitoring a CT scan image. A CT scan image may be resampled into a plurality of slices using a bilinear interpolation. A region of interest may be identified on each slice using an image processing technique. The region of interest may be masked on each slice using deep learning. Subsequently, a nodule may be detected as the region of interest using the deep learning. Further, a plurality of characteristics associated with the nodule may be identified. Furthermore, an emphysema may be detected in the region of interest on each slice. A malignancy risk score for the patient may be computed. A progress of the nodule may be monitored across subsequent CT scan images. Finally, a report of the patient may be generated.

9 Claims, 4 Drawing Sheets

(51) Int. Cl.
*G06T 5/00* (2006.01)
*G06T 7/11* (2017.01)
*G06V 10/25* (2022.01)
*G06V 10/26* (2022.01)
*G06V 10/82* (2022.01)
*G06V 10/75* (2022.01)
*A61B 6/03* (2006.01)
*A61B 6/00* (2006.01)
*G16H 30/40* (2018.01)
*G16H 50/30* (2018.01)
*G16H 50/20* (2018.01)
*G06T 7/20* (2017.01)
*G06T 7/40* (2017.01)

(52) U.S. Cl.
CPC .......... *G06V 10/273* (2022.01); *G06V 10/75* (2022.01); *G06V 10/82* (2022.01); *G16H 30/40* (2018.01); *G16H 50/20* (2018.01); *G16H 50/30* (2018.01); *G06T 2207/10081* (2013.01); *G06T 2207/20081* (2013.01); *G06T 2207/20084* (2013.01); *G06T 2207/30064* (2013.01)

(56) References Cited

U.S. PATENT DOCUMENTS

| | | |
|---|---|---|
| 2005/0207630 A1 | 9/2005 | Chan et al. |
| 2018/0338741 A1* | 11/2018 | Lyman .................. A61B 8/565 |
| 2020/0111561 A1 | 4/2020 | Lyman et al. |
| 2020/0160997 A1 | 5/2020 | Bagci et al. |
| 2020/0161005 A1* | 5/2020 | Lyman ................. G06K 9/6254 |
| 2020/0357117 A1* | 11/2020 | Lyman ................... G16H 50/20 |
| 2021/0042564 A1* | 2/2021 | Xiao .................... G06F 16/5854 |
| 2021/0118130 A1 | 4/2021 | Zhang et al. |
| 2022/0005586 A1* | 1/2022 | Brynolfsson ......... G06T 7/0012 |

* cited by examiner

MONITORING COMPUTED TOMOGRAPHY (CT) SCAN IMAGE

RELATED APPLICATIONS

This application claims priority to Indian Patent Application No. 202121045730 filed Oct. 7, 2021 in India.

TECHNICAL FIELD

The present subject matter described herein, in general, relates to a system and a method for monitoring a Computed Tomography (CT) scan image. More particularly, to monitoring a CT scan image using deep learning.

BACKGROUND

Typically, medical imaging techniques such as Computed Tomography (CT) scans and E-radiations (X-ray) scans are widely used by a health practitioner to detect lung cancers. It must be noted that an early detection of cancerous nodule is really important. Generally, the health practitioner suggests a patient to go for the CT scans when he/she diagnose a presence of nodule in the chest of the patient. Further, the health practitioner analyses the CT scans and manually identify nodules. However, the manual detection is a time consuming and a cumbersome task. At times, the health practitioner may misjudge the nodules. Also, it may happen that the nodules, which are small in size, are missed by the health practitioner.

SUMMARY

Before the present system(s) and method(s), are described, it is to be understood that this application is not limited to the particular system(s), and methodologies described, as there can be multiple possible embodiments which are not expressly illustrated in the present disclosures. It is also to be understood that the terminology used in the description is for the purpose of describing the particular implementations or versions or embodiments only and is not intended to limit the scope of the present application. This summary is provided to introduce aspects related to a system and a method for monitoring a Computed Tomography (CT) scan image. This summary is not intended to identify essential features of the claimed subject matter nor is it intended for use in determining or limiting the scope of the claimed subject matter.

In one implementation, a method for monitoring a Computed Tomography (CT) scan image is disclosed. Initially, a CT scan image of a patient may be received. Further, a gaussian smoothing method may be applied on the CT scan image to counteract noise. Subsequently, the CT scan image may be resampled into a plurality of slices. In one aspect, the CT scan image may resample using a bilinear interpolation. Upon resampling, a region of interest on each slice may be identified. In one aspect, the region of interest may be identified using an image processing technique. Further, the region of interest on each slice may be masked. In one aspect, the region of interest may be masked by removing black or air areas and fatty tissues around the region of interest using deep learning. Furthermore, a nodule may be detected as the region of interest using deep learning. Upon detection of the nodule, a plurality of characteristics associated with the nodule may be determined using the image processing technique. In one aspect, the plurality of characteristics may comprise a diameter, a calcification, a lobulation, a spiculation, a volume and a texture. Subsequently, an emphysema may be detected in the region of interest on each slice using deep learning.

Upon detection, a malignancy risk score for the patient may be computed based on the plurality of characteristics and trained data model. In one aspect, the trained data model may comprise historical data related to different diameter of nodules, different calcification of nodules, different lobulation of nodules, different spiculation of nodules, different volume of nodules, and different texture of nodules. During implementation, a progress of the nodule may be monitored over a predefined time period across subsequent CT scan images. In one aspect, the progress of the nodule may be monitored based on the diameter, a total volume of the nodule, and the malignancy risk score. Finally, a report of a patient may be generated upon monitoring the progress of the nodule. In one aspect, the report may comprise the nodule, the emphysema, the malignancy risk score, the progress of the nodule and a follow-up check with a health practitioner, thereby monitoring the CT scan image. In one aspect, the aforementioned method for monitoring the CT scan image may be performed by a processor using programmed instructions stored in a memory.

In another implementation, a non-transitory computer readable medium embodying a program executable in a computing device for monitoring a Computed Tomography (CT) scan image is disclosed. The program may comprise a program code for receiving a CT scan image of a patient. Further, the program may comprise a program code for applying a gaussian smoothing method on the CT scan image to counteract noise. Subsequently, the program may comprise a program code for resampling the CT scan image into a plurality of slices. In one aspect, the CT scan image may resample using a bilinear interpolation. Upon resampling, the program may comprise a program code for identifying a region of interest on each slice. In one aspect, the region of interest may be identified using an image processing technique. Further, the program may comprise a program code for masking the region of interest on each slice. In one aspect, the region of interest may be masked by removing black or air areas and fatty tissues around the region of interest using deep learning. Furthermore, the program may comprise a program code for detecting a nodule as the region of interest using deep learning. Upon detection of the nodule, the program may comprise a program code for determining a plurality of characteristics associated with the nodule using the image processing technique. In one aspect, the plurality of characteristics may comprise a diameter, a calcification, a lobulation, a spiculation, a volume and a texture. Subsequently, the program may comprise a program code for detecting an emphysema in the region of interest on each slice using deep learning.

Upon detection, the program may comprise a program code for computing a malignancy risk score for the patient based on the plurality of characteristics and trained data model. In one aspect, the trained data model may comprise historical data related to different diameter of nodules, different calcification of nodules, different lobulation of nodules, different spiculation of nodules, different volume of nodules, and different texture of nodules. During implementation, the program may comprise a program code for monitoring a progress of the nodule over a predefined time period across subsequent CT scan images. In one aspect, the progress of the nodule may be monitored based on the diameter, a total volume of the nodule, and the malignancy risk score. Finally, the program may comprise a program code for generating a report of a patient upon monitoring the progress of the nodule. In one aspect, the report may comprise the nodule, the emphysema, the malignancy risk score, the progress of the nodule and a follow-up check with a health practitioner, thereby monitoring the CT scan image.

BRIEF DESCRIPTION OF THE DRAWINGS

The foregoing detailed description of embodiments is better understood when read in conjunction with the appended drawings. For the purpose of illustrating of the present subject matter, an example of construction of the present subject matter is provided as figures, however, the invention is not limited to the specific method and system for monitoring a CT scan image disclosed in the document and the figures.

The present subject matter is described in detail with reference to the accompanying figures. In the figures, the left-most digit(s) of a reference number identifies the figure in which the reference number first appears. The same numbers are used throughout the drawings to refer various features of the present subject matter.

The figures depict an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "receiving," "applying" "resampling," "identifying," "masking," "determining," "detecting," "computing," "monitoring," "generating," and other forms thereof, are intended to be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art and the generic principles herein may be applied to other embodiments. However, one of ordinary skill in the art will readily recognize that the present disclosure is not intended to be limited to the embodiments described, but is to be accorded the widest scope consistent with the principles and features described herein.

The present subject matter discloses a system and a method for monitoring a CT scan image. Typically, a doctor has to manually identify nodules in the CT scan image. This is a cumbersome and a time-consuming task. More importantly, the present invention discloses a cost effective, efficient, and an automatic process for monitoring the CT scan image. The present invention generates a real-time report based on monitoring the CT scan image. Further, the present invention provides remote assessment of the CT scan image. This helps to provide consultation to a patient remotely. Initially, the CT scan image of the patient may be received. Further, a region of interest may be identified. Furthermore, a nodule and an emphysema may be detected using deep learning. The nodule may be further monitored over a predefined time period. Finally, a report of the patient may be generated upon monitoring the nodule.

While aspects of described system and method for monitoring a Computing Tomography (CT) scan image may be implemented in any number of different computing systems, environments, and/or configurations, the embodiments are described in the context of the following exemplary system.

Figure 1:
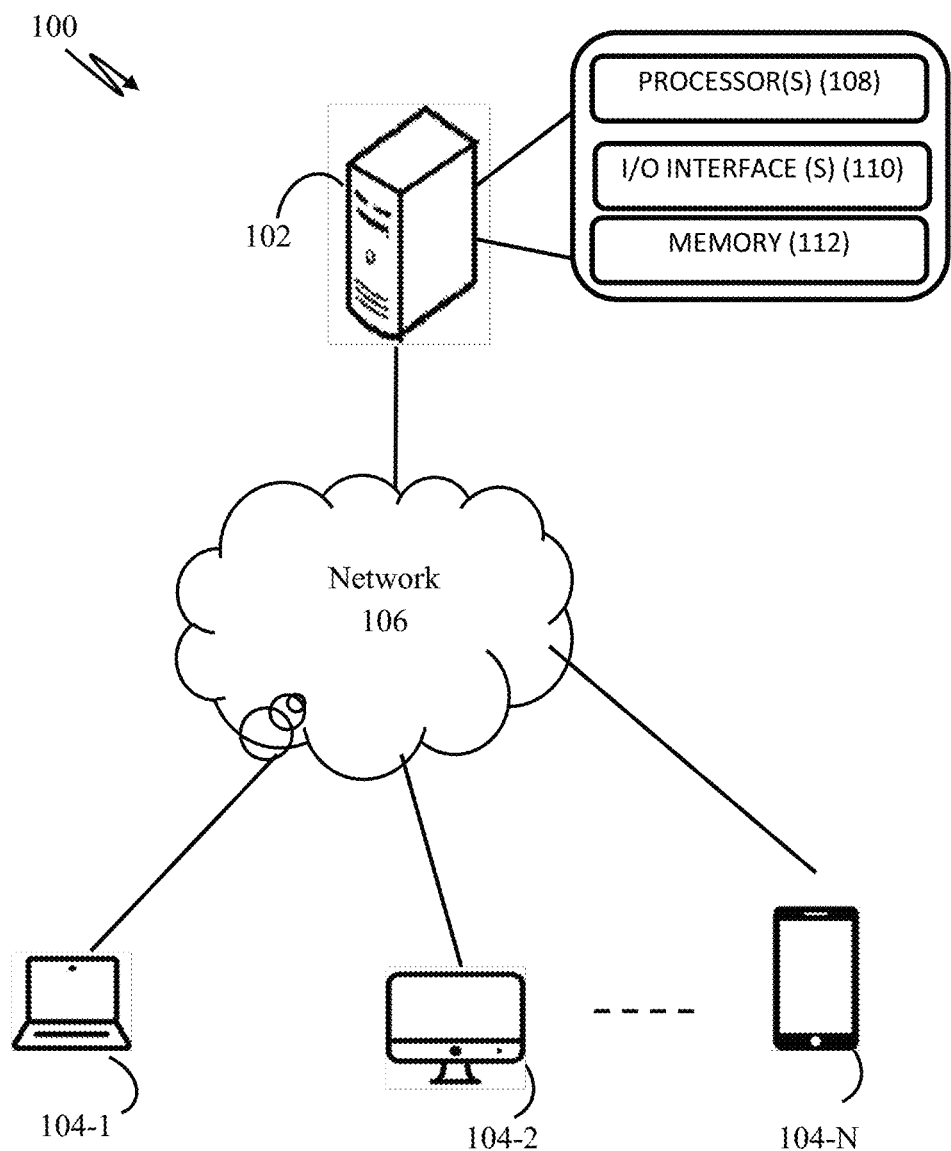
FIG. 1 illustrates a network implementation of a system for monitoring a CT scan image, in accordance with an embodiment of the present subject matter.

Referring now to FIG. 1, a network implementation 100 of a system 102 for monitoring a Computed Tomography (CT) scan image is disclosed. It may be noted that one or more users may access the system 102 through one or more user devices 104-2, 104-3 . . . 104-N, collectively referred to as user devices 104, hereinafter, or applications residing on the user devices 104. In one aspect, the one or more users may comprise a health practitioner, a doctor, a lab assistant, a radiologist and the like.

Although the present disclosure is explained considering that the system 102 is implemented on a server, it may be understood that the system 102 may be implemented in a variety of computing systems, such as a laptop computer, a desktop computer, a notebook, a workstation, a virtual environment, a mainframe computer, a server, a network server, a cloud-based computing environment. It will be understood that the system 102 may be accessed by multiple users through one or more user devices 104-1, 104-2 . . . 104-N. In one implementation, the system 102 may comprise the cloud-based computing environment in which the user may operate individual computing systems configured to execute remotely located applications. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

In one embodiment, the system 102 may include at least one processor 108, an input/output (I/O) interface 110, and a memory 112. The at least one processor 108 may be implemented as one or more microprocessors, microcomputers, microcontrollers, digital signal processors, Central Processing Units (CPUs), state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a graphical user interface, and the like. The I/O interface 110 may allow the system 102 to interact with the user directly or through the client devices 104. Further, the I/O interface 110 may enable the system 102 to communicate with other computing devices, such as web servers and external data servers (not shown). The I/O interface 110 can facilitate multiple communications within a wide variety of networks and protocol types, including wired networks, for example, LAN, cable, etc., and wireless networks, such as WLAN, cellular, or satellite. The I/O interface 110 may include one or more ports for connecting a number of devices to one another or to another server.

The memory 112 may include any computer-readable medium or computer program product known in the art including, for example, volatile memory, such as static random access memory (SRAM) and dynamic random access memory (DRAM), and/or nonvolatile memory, such as read only memory (ROM), erasable programmable ROM, flash memories, hard disks, Solid State Disks (SSD), optical disks, and magnetic tapes. The memory 112 may include routines, programs, objects, components, data structures, etc., which perform particular tasks or implement particular abstract data types. The memory 112 may include programs or coded instructions that supplement applications and functions of the system 102. In one embodiment, the memory 112, amongst other things, serves as a repository for storing data processed, received, and generated by one or more of the programs or the coded instructions.

As there are various challenges observed in the existing art, the challenges necessitate the need to build the system 102 for monitoring the CT scan image. At first, a user may use the user device 104 to access the system 102 via the I/O interface 110. The user may register the user devices 104 using the I/O interface 110 in order to use the system 102. In one aspect, the user may access the I/O interface 110 of the system 102. The detail functioning of the system 102 is described below with the help of figures.

The present subject matter describes the system 102 for monitoring the CT scan image. The system 102 may monitor the CT scan image in real-time. The CT scan image may be monitored using deep learning and image processing technique. In order to monitor the CT scan image, initially, the system 102 may receive the CT scan image of a patient. In one aspect, the CT scan image may be referred as a chest CT scan. The CT scan image may be a three-dimensional image.

In one aspect, the CT scan image may be a Non-contrast CT series with axial cuts and soft reconstruction kernel which covers an entire Lung. The CT scan image may be one non-contrast CT series with consistently spaced axial slices. The CT scan image may comprise minimum of 40 axial slices in the series. The CT scan image may be available in a Digital Imaging and Communications in Medicine (DICOM) format. In one example, a maximum thickness of the CT scan image may be 6 mm.

In one embodiment, the system 102 may check if the CT scan image is not a Chest CT scan or if there is no plain axial series, then the CT scan image may not be processed further. The system 102 may transmit a response to the user indicating that the uploaded series or the CT scan image is not a valid.

In one embodiment, the system 102 may comprise a trained data model. The trained data model may comprise historical data related to previous CT scans of the patient, one or more CT scans associated with a set of patients and the like. In one example, the trained data model may comprise dataset containing 120,000 Chest CTs used for training and internally validating algorithms. The dataset may be referred to as 'development dataset'. The development dataset may be divided into training dataset and internal validation dataset using a 4:1 split. The resultant validation dataset (20% of the entire data) may be used to estimate the performance of the trained data model and for hyper-parameter tuning. The splitting may be based on a patient identity (ID) eliminating any spillage between the training and the validation splits.

In one aspect, the dataset in the trained data model may be large and valid that results into multiple advantages. The dataset may comprise an adequate number of scans for all target abnormalities, allowing the development of accurate algorithm. An adequate number of control scans with various non-target abnormalities and normal variations may be likely to be present in the dataset. It may reduce the chances that these occurrences will negatively impact performance when the algorithm is deployed in the real world on previously unseen data. The selection of a large number of sources for the training data, rather than a large amount of data from a single site, may be advantageous because it allows the algorithms to be trained on the CT scan images from a wide variety of device manufacturers and CT protocols, without explicitly specifying.

In one embodiment, the system 102 may automate the checking of the DICOM for age, body part, contrast/non-contrast, slice thickness, view, and kernel. The system 102 may use a separate module called a series classifier which is described in detail in the preprocessing section. Further, the system 102 may check presence of a corresponding radiology report i.e., a ground truth, by matching the patient IDs. If no report is found, the CT scan image may be excluded. Subsequently, the system 102 may automate the checking of radiology report for the age. The system 102 may identify a number of cases which are labelled as CHEST in the DICOM attribute but are not actually Chest CT scan images, such CT scan images may be identified using the trained series classifier and not used in training or testing (these can be considered outliers).

In one embodiment, only requirements for training the system 102 may be the presence of the DICOM data and a text report. Once these requirements are met, the concept of missing values or missing data may not apply as it does for other machine learning algorithms. There may be no other exclusions from the training dataset.

In order to eliminate the possibility of data/label leakage, the training and the validation split may be performed using a randomization procedure at the patient level rather than at the Study level. The Chest CT scan image studies from an (de-identified) individual may be placed either in the training set or the testing set, but not both. There may be no train-test contamination as the sources of data that were used for train data are completely different to those used for collecting test data. There may be no validation data contamination as the training and the validation split is done based on the hash of a unique identifier. The input data is an image i.e., the CT scan image whereas the target variable is a binary output i.e., information related to the presence of a particular abnormality is not encoded in the actual image. In one example, an abnormal Chest CT scan image may not have any explicit information that it is abnormal apart from features in the image data.

In one aspect, an automated natural language processing based labeling approach may be chosen as the primary method for generating the ground truth. Additionally, a number of pixel-level hand annotations may be used to either further improve accuracy or to provide input to a segmentation algorithm. It may be noted that an intended use of the system 102 is to aid in the interpretation of the Chest CT images, therefore the labeling method that largely depends on the radiology reports, which are the ground truth for these images, is appropriate.

Each Chest CT scan image in the training dataset may have a single corresponding the ground truth, generated during the normal course of clinical care. The ground truth includes at least the radiology report and a biopsy report where available. The ground truth is used for training the algorithm. The radiologist reports may not be generated specifically for the purpose of training the system 102 but may be obtained retrospectively from anonymized clinical records. The source of the reports may be exactly the same as the source of the CT scan images. In one example, the qualifications of the radiologists who generated these reports may be one of—MD, Radiology: Doctor of Medicine in Radiology, DNB, Radiology: Diplomate of National Board, Radiology, and DMRD: Diploma in Medical Radio Diagnosis.

In one aspect, the report may be in a free text format, and a custom Natural Language Processing (NLP) algorithm may be used to extract labels corresponding to each of the abnormal findings (indications). The labels may be served as the ground truth. The NLP algorithm may use well-established systems developed to manage typographic errors, detect negations and identify synonyms.

The Natural Language Processing (NLP) algorithms may be developed based on rules/dictionaries, trained with machine learning techniques, or a combination of the two approaches. Rule based NLP algorithm may use a list of manually created rules to parse the unorganized content and structure it. Machine Learning (ML) based NLP algorithm, on the other hand, may automatically generate the rules when trained on a large annotated dataset. The rule-based NLP algorithm may be chosen over a machine-learning based NLP algorithm for the purpose of labeling radiology reports.

The rule-based NLP algorithm may have few advantages comprising clinical knowledge can be manually incorporated into the rule-based NLP algorithm. In order to capture this knowledge in the ML based algorithm, a huge amount of annotation may be required. Further, rules may be readily added or modified to accommodate a new set of target findings in the rule-based NLP algorithm.

Once the CT scan image is received, the system 102 may apply a gaussian smoothing method on the CT scan image. The gaussian smoothing method may be configured to counteract noise. In other words, the gaussian smoothing method may reduce image noise and enhance a structure of the CT scan image. In one aspect, the gaussian smoothing may be applied in a z dimension (i.e., longitudinal axis). In one example, a gaussian kernel used for the gaussian smoothing may have a sigma of 1 mm in the z dimension, and 0 in other dimensions. The gaussian smoothing may have a negligible effect on the CT scan image with thickness greater than 2 mm as the gaussian kernel decays by 95% at 2*sigma (=2 mm).

Subsequently, the system 102 may resample the CT scan image into a plurality of slices. The CT scan image may be resampled using a bilinear interpolation. The bilinear interpolation may use the distance weighted average of the four nearest pixel values to estimate a new pixel value. In one aspect, the system 102 may resample the CT scan image so that its slice thickness is around 2.5 mm. The system 102 may obtain a resampling factor by dividing 2.5 by the series' slice thickness and rounding the result to an integer. The rounding may be used to ensure that there are no resampling artifacts.

Further, the system 102 may identify a region of interest on each slice. The region of interest may be identified using an image processing technique. In one aspect, the region of interest may indicate an abnormality on each slice. In one example, the region of interest may correspond to possible nodules on each slice.

In one embodiment, a small part of the CT scan image may be annotated at a pixel level which serve as the secondary labels to the training algorithms. It may include the region of interest annotation (lung, diaphragm, mediastinum and ribs) as well as abnormality pixel-wise annotation which are then used to derive the Region of Interest (ROI) level annotations. In one example, 5% of the Chest CT scan images may be duplicated, as a test for competency of the annotators. If there was less than 75% concordance the CT scan image was re-annotated. These discrepancies may be tracked as a way to continually test the accuracy of the annotations and the competency of the annotators.

Once the region of interest is identified, the system 102 may mask the region of interest on each slice. In one aspect, the region of interest may be masked by removing black or air areas and fatty tissues around the region of interest. The region of interest may be masked using deep learning.

In one embodiment, each slice, from the plurality of slices, may consist of a significant amount of black or air areas and fatty tissue around the region of interest. These areas may not be necessary to evaluate the slice. Removing these areas may help to focus on the region of interest. The masking may help to improve performance of a detection algorithm.

In one aspect, the system 102 may compute a three-dimensional bounding box around the masked region. The bounding box may be used to crop the slice. The mask may be computed using a separately trained 2D UNet segmentation algorithm.

Subsequently, the system 102 may detect a nodule as the region of interest. The nodule may be detected using the deep learning. In one aspect, the nodule may be present in multiple slices. A total number of slices in which the nodule is present may be computed.

In one aspect, the system 102 may comprise a Se-ResNeXt50 model to detect the nodule. The Se-ResNeXt50 may be a modified version of ResneXt 50 a popular neural network architecture which has 50 layers with increased inter layer connectivity. The model may have 50 convolutional layers, modified to take in regional information and softmax based confidences. Further, the system 102 may comprise U-Net and FPN. The U-Net and FPN may be a popular segmentation architecture for biomedical segmentation. The U-Net and FPN may have five downsampling and five upsampling blocks of convolutional layers with skip connections.

Figure 2:
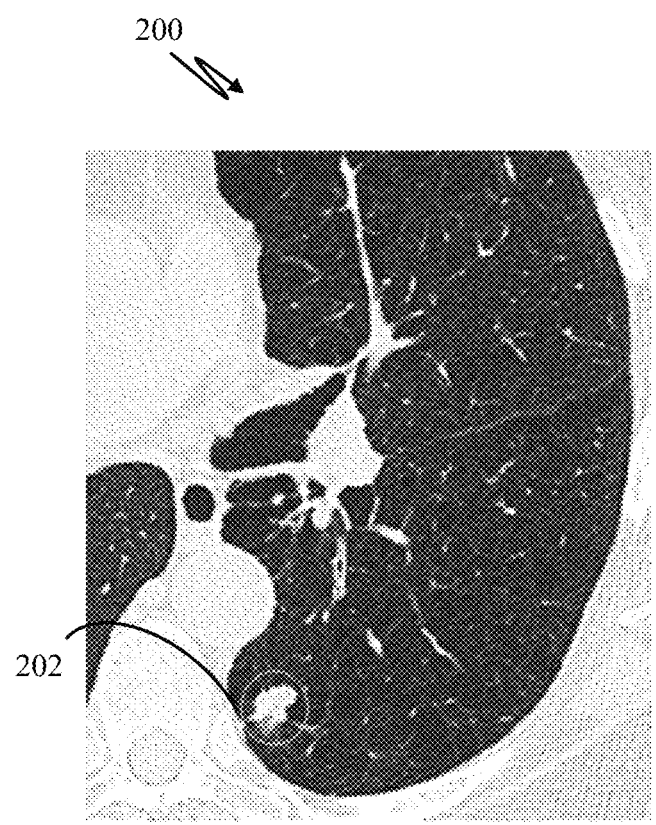
FIG. 2 shows a structure of a nodule, in accordance with an embodiment of the present subject matter.

Referring now to FIG. 2, the structure of the nodule is shown, in accordance with an embodiment of the present subject matter. In one embodiment, the CT scan image 200 of the patient may be received. Further, the system 102 may detect the nodule 202. In one example, the nodule may be a rounded or irregular opacity, well or poorly defined, measuring up to 3 cm in the diameter.

In one embodiment, the system 102 may use the neural network architecture for slice-wise inference. It is an FPN with SE-ResNext-50 backbone with classification and segmentation heads. Weights of the Convolutional Neural Network (CNN) may be used to process each slice may be 'tied' and thus share the same weights.

Slice level classification output may be pooled into scan level output using following operation as shown in equation 1.

$$P\text{scan} = \Sigma i = 0 \text{ to \#slices } w_i * P\text{slice}i \qquad \text{Equation 1}$$

Wherein $w_i$ may be softmax weights computed as shown in equation 2.

$$wi = \exp(P\text{slice}i)/\Sigma i = 0 \text{ to \#slices} \exp(P\text{slice}i) \qquad \text{Equation 2}$$

In one aspect, essentially the system 102 may comprise a softer version of max pooling used in CNNs. The operation may be referred as 'softmaxpooling'. The model architecture may comprise three outputs: scan-level probability, list of slice-level probabilities of presence of nodules and a 3D segmentation mask of nodules.

Referring again to FIG. 1, the system 102 may determine a plurality of characteristics associated with the nodule. The plurality of characteristics may be identified using the image processing technique. The plurality of characteristics may comprise a diameter, a calcification, a lobulation, a spiculation, a texture, a volume and the like. In one aspect, the diameter may correspond to a size. The calcification may indicate an amount of calcium present. The lobulation may indicate a location. The spiculation may indicate a border. In one embodiment, the system 102 may use a Convolution Neural Network (CNN) module to determine the plurality of characteristics. In one example, the diameter of the nodule may be further used to determine a total volume of the nodule and an area covered by the nodule.

Further, the system 102 may detect an emphysema in the region of interest. The emphysema may be detected using the deep learning. In one example, the system 102 may comprise a detection module to detect the nodule and/or the emphysema. In one embodiment, the system 102 may comprise SE-ResNet18 model to detect the emphysema on each slice. The Se-Resnet-18 model may be a modified version of Resnet 18 architecture with more inter layer connectivity to increase capacity to learn. The model may have same 18 layers as Resnet-18. The model may be slightly modified to take in regional information and modified SoftMax based confidences.

Further, the system 102 may comprise U-Net and FPN. The U-Net and FPN may be a popular segmentation architecture for biomedical segmentation. The U-Net and FPN may have five downsampling and five upsampling blocks of convolutional layers with skip connections.

Figure 3:
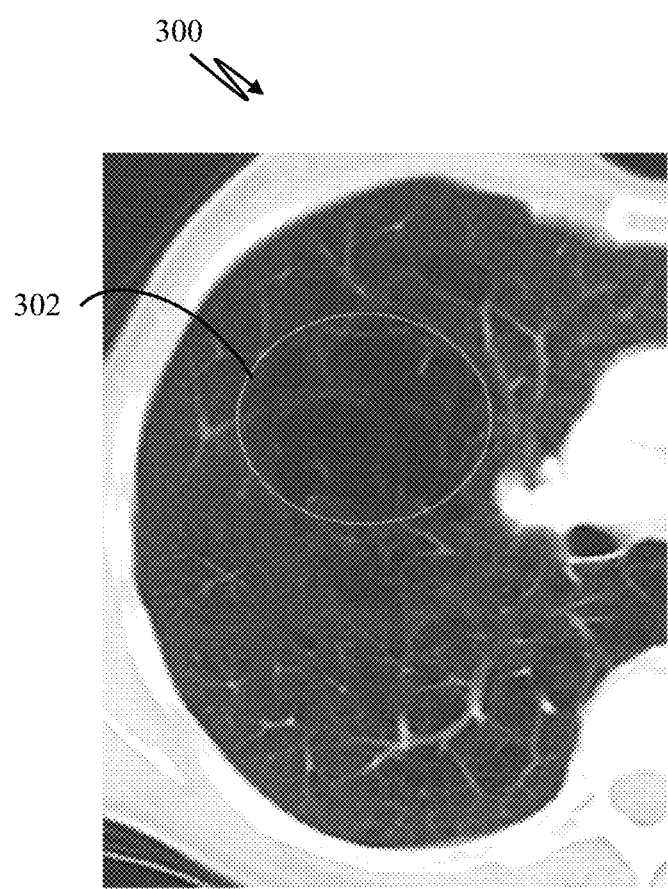
FIG. 3 shows a structure of an emphysema, in accordance with an embodiment of the present subject matter.

Referring now to FIG. 3, a structure of the emphysema is shown, in accordance with an embodiment of the present subject matter. In one embodiment, the CT scan image 300 may be received. Further, the emphysema 302 may be detected. The emphysema 302 may be a permanently enlarged airspaces distal to the terminal bronchiole with destruction of alveolar walls. On the CT scan image, an appearance of the emphysema 302 may consist of focal areas or regions of low attenuation, usually without visible walls.

Referring again to FIG. 1, the deep learning may be used to detect the nodule and/or the emphysema. The deep learning is a form of a machine learning technique where the hypothesis set is composed of neural networks i.e., Convolutional Neural Networks (CNN. Once the trained data model using the CNN is generated, the system may be locked, tested and deployed.

In one embodiment, the CNN or ConvNet is a class of deep neural networks, most commonly applied to analyzing visual images. Neural networks may be composed of a large number of interconnected individual computational units, arranged in layers, each of which applies a learned function to the input data. CNN may be used for image processing and may be characterized by 'convolution' layers, which contain layers that learn the matrix operations required to efficiently process images.

In the embodiment, an output of the CNN may be a score between 0 and 1. When trained appropriately with a large dataset of images and the corresponding ground truth, the CNN may output the probability that a given image belongs to a certain class or contains a specific abnormality i.e., the nodule or the emphysema. The output of the nodule detection algorithm may be a bounding box that localizes the region of interest.

In the embodiment, the detection module may use a two-dimensional classification convolutional neural network trained to output the probability or heatmap that an abnormality is present in each slice. The slice level probability or heatmaps may be processed using a pooling operation for both abnormalities along with an additional 3D CNN for lung nodules to reduce false positives.

In one aspect, the system 102 may resize each slice using bilinear interpolation. Each slice may be resized based on the detection of abnormality i.e., the nodule or the emphysema. In one example, for the nodule, the standard size may include pixel size (320, 320) slices for initial network, 96×96×96 patches around median point of proposal for FP reduction. Further, for the emphysema, the standard size may include the pixel size (224, 224).

Upon detection, the system 102 may compute a malignancy risk score for the patient. The malignancy risk score may be computed based on the plurality of characteristics and the trained data model. The malignancy risk score may indicate if the nodule is malignant i.e., cancerous or not.

In one aspect, the trained data model may comprise historical data related to different diameter of nodules, different calcification of nodules, different lobulation of nodules, different spiculation of nodules, different texture of nodules different volume of nodules, and the like. In one example, the historical data may comprise previous clinical reports associated with a set of patients. The trained data model may be generated based on continuously learning data associated with the set of patients using the deep learning. The trained data model may enable an accurate analysis.

In one embodiment, the system 102 may compare the plurality of characteristics with the historical data. In one aspect, the system 102 may use a Convolutional Neural Network (CNN) model for the comparison. In one example, the diameter may be compared with the different diameter of nodules. The calcification may be compared with the different calcification of nodules. The lobulation may be compared with the different lobulation of nodules. The spiculation may be compared with the different spiculation of nodules. The texture may be compared with the different texture of nodules. Based on the comparison, the system 102 may computer the malignancy risk score for the patient. The malignancy risk score may be computed in real-time.

In another embodiment, the system 102 may assign a weightage to each characteristic. Further, the weightage and the plurality of characteristics may be used to compute the malignancy risk score.

Subsequently, the system 102 may monitor a progress of the nodule over a predefined time period. The progress of the nodule may be monitored across subsequent CT scan images. The progress of the nodule may be monitored based on the diameter, the total volume of the nodule, the malignancy risk score and the like. The progress of the nodule may be monitored in real-time.

In one embodiment, the diameter may be compared with the different dimeters of nodules. Further, the malignancy risk score may be compared with a predefined threshold score. The total volume of the nodule may be compared with a previous volume stored in the trained data model. In one aspect, a Convolution Neural Network (CNN) may be used to perform the comparison. Based on the comparison, the system 102 may determine the progress of the nodule. In one example, the system 102 may predict the progress of the module based on the malignancy risk score and the predefined threshold score.

Further, the system 102 may generate a report of the patient upon monitoring the progress of the nodule. The report may be generated in real-time. The report may comprise the nodule, the emphysema, the malignancy risk score, the progress of the nodule and a follow-up check with a health practitioner. In one aspect, the health practitioner may analyze the report and provide consultation to the patient remotely. In one aspect, the system 102 may notify the patient regarding the follow-up check with a health practitioner. The follow-up check may be notified based on the malignancy risk score, the progress of the nodule and the like.

In one embodiment, the system 102 may comprise a false positive detection module. The false detection module may determine false positive nodules on each slice. The false positive nodules may be determined using a 3-dimentional CNN model. The false positive nodules may be determined by comparing the nodules with the trained data model. In one embodiment, the system 102 may use the lobulation and the diameter to determine the false positive nodules.

In one aspect, for the nodule, the system 102 may calculate a median point. Further, a 3D patch of dimension 96×96×96 with the median point as the Centre may be extracted from the CT scan image (resampled such that 1 voxel=1 mm3). The patch may be processed using a 3D SE-ResNet18 trained to classify patches into whether or not they contain nodule(s). In one embodiment, training data for the false positive reduction module may be synthesized by accumulating negative patches using random sampling from normal Chest CT scan image s and positive patches using pixel/ROI level annotations by experts.

In one embodiment, the system 102 may receive the CT scan image which is further processed through an API is first passed to a scan filtering and series picking module. The scan filtering and series picking module may examine each series to determine if there is a plain i.e., non-contrast axial series of the Chest CT scan image present. The plain axial series may be further passed to an image reading module before sending the CT scan image to an abnormality-specific preprocessing modules and models. The scan filtering and series picking module may check the DICOM tags on each series to determine if the series is CT Chest plain axial series.

In one embodiment, an Image reading module may take in the plain axial series from the scan filtering and series picking module. Further, a series of raw dicom files, each representing a slice, may be needed to be read and aggregated into the three-dimensional image. Therefore, sorting of the slices may be important while reading dicom files. The DICOM tag Image Position Patient may be used to sort the dicom files when available and the software falls back to the dicom tag Instance Number when not available. In one aspect, the open-source medical image processing library SimpleITK6 is used to implement the image reading module.

In one aspect, the dicom tag and the tag description may be provided in the Table 1.

TABLE 1

Dicom tag and tag description

| DICOM tag used for series selection | Tag description |
| --- | --- |
| Study Description | Institution-generated description or classification of the Study (component) performed. |
| Series Description | Description of the Series |
| Modality | Type of equipment that originally acquired the data used to create the images in this Series. |
| Body Part Examined | Text description of the part of the body examined. |
| Image Orientation Patient | The direction cosines of the first row and the first column with respect to the patient. |
| Image Position Patient | The x, y, and z coordinates of the upper left hand corner (centre of the first voxel transmitted) of the image, in mm. |
| Pixel Spacing | Physical distance in the patient between the centre of each pixel, specified by a numeric pair - adjacent row spacing (delimiter) adjacent column spacing in mm. |
| Slice Location | Relative position of the image plane expressed in mm. |
| Slice Thickness | Nominal slice thickness, in mm. |
| Rows | Number of rows in the image. |
| Columns | Number of columns in the image. |
| Image Type | Image identification characteristics. See Section C.7.6.1.1.2 of dicom standard for Defined Terms and further explanation. |
| Convolution Kernel | A label describing the convolution kernel or algorithm used to reconstruct the data |
| Window Centre | Window Centre for display. |
| Window Width | Window Width for display. |
| Contrast Bolus Agent | Contrast or bolus agent |
| Contrast Bolus Route | Administration route of contrast agent |
| Requested Contrast Agent | Contrast agent requested for use in the Scheduled Procedure Step |
| Manufacturer | Manufacturer of the equipment that produced the Composite Instances. |

Figure 4:
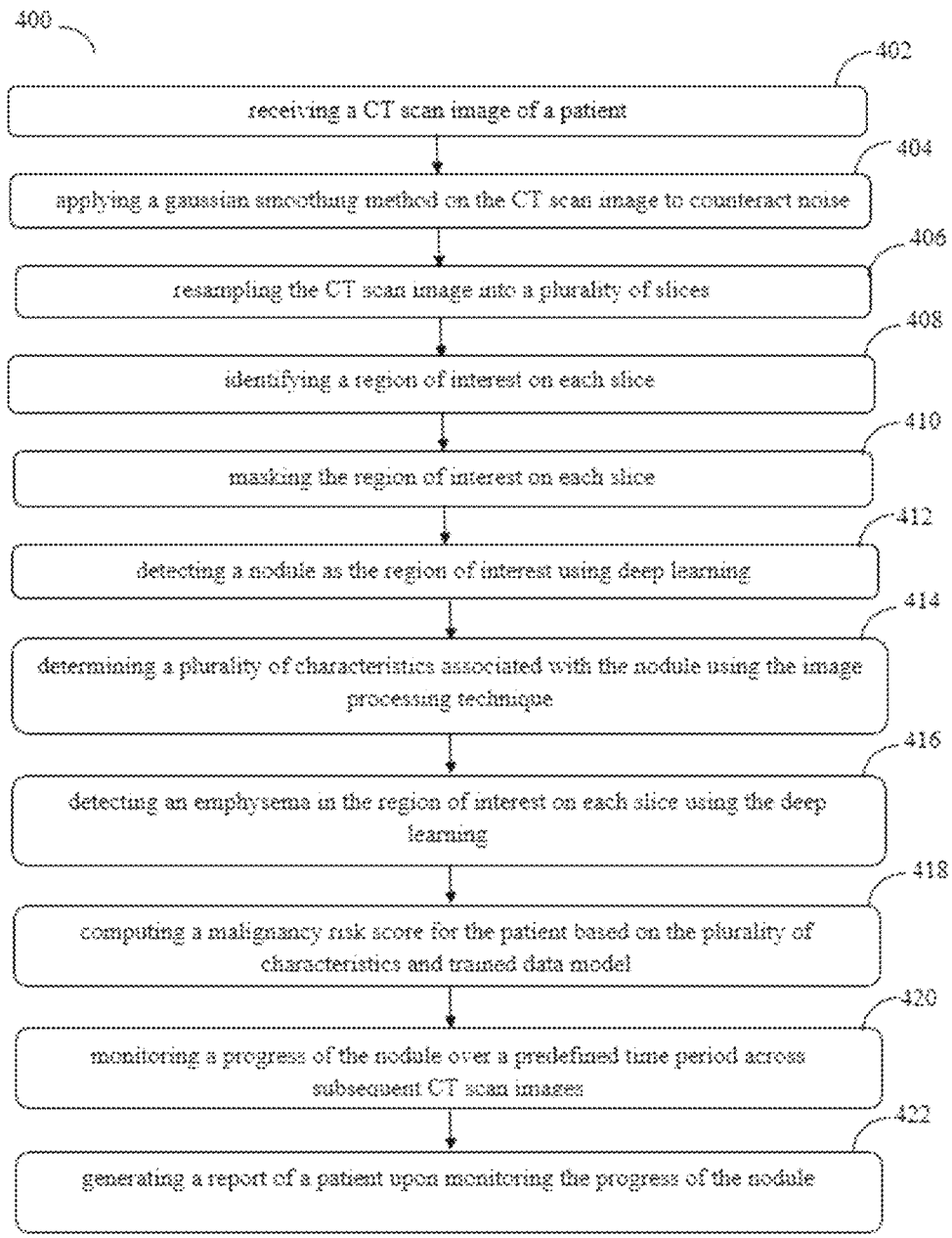
FIG. 4 illustrates a method for monitoring a CT scan image, in accordance with an embodiment of the present subject matter.

Referring now to FIG. 4, a method 400 for monitoring a CT scan image is shown, in accordance with an embodiment of the present subject matter. The method 400 may be described in the general context of computer executable instructions. Generally, computer executable instructions can include routines, programs, objects, components, data structures, procedures, modules, functions, etc., that perform particular functions or implement particular abstract data types.

The order in which the method 400 is described is not intended to be construed as a limitation, and any number of the described method blocks can be combined in any order to implement the method 400 or alternate methods for monitoring the CT scan image. Additionally, individual blocks may be deleted from the method 400 without departing from the spirit and scope of the subject matter described herein. Furthermore, the method 400 for monitoring CT scan image can be implemented in any suitable hardware, software, firmware, or combination thereof. However, for ease of explanation, in the embodiments described below, the method 400 may be considered to be implemented in the above-described system 102.

At block 402, a CT scan image of a patient may be received.

At block 404, a gaussian smoothing method may be applied on the CT scan image to counteract noise.

At block 406, the CT scan image may be resampled into a plurality of slices. In one aspect, the CT scan image may be resampled using a bilinear interpolation.

At block 408, a region of interest may be identified. In one aspect, the region of interest may be identified using an image processing technique.

At block 410, the region of interest may be masked on each slice. In one aspect, the region of interest may be masked by removing black or air areas and fatty tissues around the region of interest using deep learning.

At block 412, a nodule as the region of interest may be identified using the deep learning.

At block 414, a plurality of characteristics associated with the nodule may be determined using the image processing technique. In one aspect, the plurality of characteristics may comprise a diameter, a calcification, a lobulation, a spiculation, a volume and a texture.

At block 416, an emphysema may be detected in the region of interest on each slice using the deep learning.

At block 418, a malignancy risk score for the patient may be computed based on the plurality of characteristics and trained data model. In one aspect, the trained data model may comprise historical data related to different diameter of nodules, different calcification of nodules, different lobulation of nodules, different spiculation of nodules, different volume of nodules, and different texture of nodules.

At block 420, a progress of the nodule may be monitored over a predefined time period across subsequent CT scan images. In one aspect, the progress of the nodule may be monitored based on the diameter, a total volume of the nodule and the malignancy risk score.

At block 422, a report of the patient may be generated upon monitoring the progress of the nodule. In one aspect, the report may comprise the nodule, the emphysema, the malignancy risk score, the progress of the nodule and a follow-up check with a health practitioner, thereby monitoring the CT scan image.

Exemplary embodiments discussed above may provide certain advantages. Though not required to practice aspects of the disclosure, these advantages may include those provided by the following features.

Some embodiments of the system and the method enable monitoring a CT scan image using deep learning and image processing technique.

Some embodiments of the system and the method enable detecting a nodule and an emphysema using a Convolution Neural Network (CNN) model.

Some embodiments of the system and the method enable identifying false positive nodules using a 3-dimentional CNN model.

Some embodiments of the system and the method enable computing a malignancy risk score using a plurality of characteristics.

Some embodiments of the system and the method enable an increase in speed of process for monitoring of the CT scan image.

Some embodiments of the system and the method enable an efficient and an accurate process using the large dataset.

Although implementations for methods and system for monitoring a CT scan image have been described in language specific to structural features and/or methods, it is to be understood that the appended claims are not necessarily limited to the specific features or methods described. Rather, the specific features and methods are disclosed as examples of implementations for monitoring the CT scan image.

What is claimed is:

1. A method for monitoring a Computed Tomography (CT) scan image, the method comprising:
    receiving, by a processor, a CT scan image of a patient;
    applying, by the processor, a gaussian smoothing method on the CT scan image to counteract noise;
    resampling, by the processor, the CT scan image into a plurality of slices, wherein the CT scan image is resampled using a bilinear interpolation;
    identifying, by the processor, a region of interest on each slice, wherein the region of interest is identified using an image processing technique;
    masking, by the processor, the region of interest on each slice, wherein the region of interest is masked by removing black or air areas and fatty tissues around the region of interest using deep learning;
    detecting, by the processor, a nodule as the region of interest using the deep learning, wherein the nodule is detected upon the masking of the region of interest;
    determining, by the processor, a plurality of characteristics associated with the nodule using the image processing technique, wherein the plurality of characteristics comprise a diameter, a calcification, a lobulation, a spiculation, a volume, and a texture;
    detecting, by the processor, an emphysema in the region of interest on each slice using the deep learning;
    computing, by the processor, a malignancy risk score for the patient in real-time based on the plurality of characteristics and trained data model, wherein the trained data model comprises historical data related to different diameter of nodules, different calcification of nodules, different lobulation of nodules, different spiculation of nodules, different volume of nodules, and different texture of nodules, and wherein the malignancy risk score is dependent on a weightage of each characteristic;
    monitoring, by the processor, a progress of the nodule in real-time over a predefined time period across subsequent CT scan images, wherein the progress of the nodule is monitored based on the diameter, a total volume of the nodule and the malignancy risk score; and
    generating, by the processor, a report of the patient upon monitoring the progress of the nodule, wherein the report comprises the nodule, the emphysema, the malignancy risk score, the progress of the nodule and a follow-up check with a health practitioner, thereby monitoring the CT scan image.

2. The method as claimed in claim 1, further comprises resizing each slice using a bilinear interpolation.

3. The method as claimed in claim 1, further comprises predicting the progress of the module based on the malignancy risk score and a predefined threshold score.

4. The method as claimed in claim 1, further comprises determining false positive nodules on each slice using a 3-dimentional CNN model, wherein the false positive nodules are determined by comparing the nodules with the trained data model.

5. A system for monitoring a Computed Tomography (CT) scan image, the system comprising:
   a memory; and
   a processor coupled to the memory, wherein the processor is configured to execute instructions stored in the memory to:
      receive a CT scan image of a patient;
      apply a gaussian smoothing method on the CT scan image to counteract noise;
      resample the CT scan image into a plurality of slices, wherein the CT scan image is resampled using a bilinear interpolation;
      identify a region of interest on each slice, wherein the region of interest is identified using an image processing technique;
      mask the region of interest on each slice, wherein the region of interest is masked by removing black or air areas and fatty tissues around the region of interest using deep learning;
      detect a nodule as the region of interest using the deep learning, wherein the nodule is detected upon the masking of the region of interest;
      determine a plurality of characteristics associated with the nodule using the image processing technique, wherein the plurality of characteristics comprise a diameter, a calcification, a lobulation, a spiculation, a volume, and a texture;
      detect an emphysema in the region of interest on each slice using the deep learning;
      compute a malignancy risk score for the patient in real-time based on the plurality of characteristics and trained data model, wherein the trained data model comprises historical data related to different diameter of nodules, different calcification of nodules, different lobulation of nodules, different spiculation of nodules, different volume of nodules, and different texture of nodules, and wherein the malignancy risk score is dependent on a weightage of each characteristic;
      monitor a progress of the nodule in real-time over a predefined time period across subsequent CT scan images, wherein the progress of the nodule is monitored based on the diameter, a total volume of the nodule and the malignancy risk score; and
      generate a report of the patient upon monitoring the progress of the nodule, wherein the report comprises the nodule, the emphysema, the malignancy risk score, the progress of the nodule and a follow-up check with a health practitioner, thereby monitoring the CT scan image.

6. The system as claimed in claim 5, further configured to resize each slice using a bilinear interpolation.

7. The system as claimed in claim 5, further configured to predict the progress of the module based on the malignancy risk score and a predefined threshold score.

8. The system as claimed in claim 5, further configured to determine false positive nodules on each slice using a 3-dimentional CNN model, wherein the false positive nodules are determined by comparing the nodules with the trained data model.

9. A non-transitory computer program product having embodied thereon a computer program for monitoring a Computed Tomography (CT) scan image, the computer program product storing instructions, the instructions comprising instructions for:
   receiving a CT scan image of a patient;
   applying a gaussian smoothing method on the CT scan image to counteract noise;
   resampling the CT scan image into a plurality of slices, wherein the CT scan image is resampled using a bilinear interpolation;
   identifying a region of interest on each slice, wherein the region of interest is identified using an image processing technique;
   masking the region of interest on each slice, wherein the region of interest is masked by removing black or air areas and fatty tissues around the region of interest using deep learning;
   detecting a nodule as the region of interest using the deep learning, wherein the nodule is detected upon the masking of the region of interest;
   determining a plurality of characteristics associated with the nodule using the image processing technique, wherein the plurality of characteristics comprise a diameter, a calcification, a lobulation, a spiculation and a texture;
   detecting an emphysema in the region of interest on each slice using the deep learning;
   computing a malignancy risk score for the patient in real-time based on the plurality of characteristics and trained data model, wherein the trained data model comprises historical data related to different diameter of nodules, different calcification of nodules, different lobulation of nodules, different spiculation of nodules, different volume of nodules, and different texture of nodules, and wherein the malignancy risk score is dependent on a weightage of each characteristic;
   monitoring a progress of the nodule in real-time over a predefined time period across subsequent CT scan images, wherein the progress of the nodule is monitored based on the diameter, a total volume of the nodule and the malignancy risk score; and
   generating a report of the patient upon monitoring the progress of the nodule, wherein the report comprises the nodule, the emphysema, the malignancy risk score, the progress of the nodule and a follow-up check with a health practitioner, thereby monitoring the CT scan image.

* * * * *